US010916015B2

(12) United States Patent
Ren

(10) Patent No.: US 10,916,015 B2
(45) Date of Patent: Feb. 9, 2021

(54) SEGMENTATION IN OPTICAL COHERENCE TOMOGRAPHY IMAGING

(71) Applicant: Alcon Inc., Fribourg (CH)

(72) Inventor: Hugang Ren, Cypress, CA (US)

(73) Assignee: Alcon Inc., Fribourg (CH)

( * ) Notice: Subject to any disclaimer, the term of this patent is extended or adjusted under 35 U.S.C. 154(b) by 39 days.

(21) Appl. No.: 16/199,423

(22) Filed: Nov. 26, 2018

(65) Prior Publication Data

US 2019/0164294 A1 May 30, 2019

Related U.S. Application Data

(60) Provisional application No. 62/592,497, filed on Nov. 30, 2017.

(51) Int. Cl.
*A61B 3/10* (2006.01)
*G06T 7/174* (2017.01)
*G06T 7/12* (2017.01)
*G06T 5/50* (2006.01)
*G06T 7/11* (2017.01)

(52) U.S. Cl.
CPC .............. *G06T 7/174* (2017.01); *A61B 3/102* (2013.01); *G06T 5/50* (2013.01); *G06T 7/11* (2017.01); *G06T 7/12* (2017.01); *G06T 2207/10056* (2013.01); *G06T 2207/10101* (2013.01); *G06T 2207/20192* (2013.01); *G06T 2207/20224* (2013.01); *G06T 2207/30041* (2013.01)

(58) Field of Classification Search
CPC . G06T 2207/10101; G06T 2207/30041; G06T 7/0012; G06T 5/50; G06T 7/10; G06T 7/12; G06T 7/60; G06T 2207/10056; G06T 2207/10132; G06T 2207/20024; G06T 2207/20192; G06T 7/0016; G06T 7/11; G06T 7/13; G06T 7/174; G06T 7/143; G06T 7/33; A61B 5/0066; A61B 3/102; A61B 3/10; A61B 3/0025; A61B 3/1225; A61B 3/0008
See application file for complete search history.

(56) References Cited

U.S. PATENT DOCUMENTS

| 2007/0263227 A1* | 11/2007 | Mujat ...................... G06T 7/12 356/511 |
| 2008/0100612 A1* | 5/2008 | Dastmalchi .......... A61B 3/0058 345/418 |
| 2009/0268159 A1* | 10/2009 | Xu .......................... A61B 3/14 351/206 |

(Continued)

FOREIGN PATENT DOCUMENTS

WO    2017/098388 A1    6/2017

*Primary Examiner* — Allahyar Kasraian

(57) ABSTRACT

A method for improving segmentation in optical coherence tomography imaging. The method comprises obtaining an OCT image of imaged tissue, generating a first feature image for at least a portion of the OCT image, and generating a second feature image for at least the portion of the OCT image, based on either the OCT image or the first feature image, by integrating image data in a first direction across the OCT image or first feature image. A third feature image is generated as a mathematical function of the first and second feature images, and layer segmentation for the OCT image is performed, based on the third feature image.

8 Claims, 9 Drawing Sheets

(56) References Cited

U.S. PATENT DOCUMENTS

| | | | |
|---|---|---|---|
| 2012/0140179 A1* | 6/2012 | Miyasa | A61B 3/102 351/206 |
| 2012/0274897 A1 | 11/2012 | Narashimha-Iyer et al. | |
| 2013/0301008 A1* | 11/2013 | Srivastava | G06T 7/20 351/246 |
| 2015/0062590 A1* | 3/2015 | Bagherinia | G06T 7/10 356/479 |
| 2016/0307314 A1* | 10/2016 | Reisman | G06K 9/52 |
| 2016/0317027 A1* | 11/2016 | Goto | A61B 3/102 |
| 2017/0209037 A1* | 7/2017 | Sumiya | A61B 3/1025 |
| 2017/0221203 A1* | 8/2017 | Iwase | G06T 7/0012 |
| 2018/0014725 A1* | 1/2018 | Bagherinia | A61B 3/102 |
| 2018/0192866 A1* | 7/2018 | Abou Shousha | G06T 3/0068 |
| 2019/0108636 A1* | 4/2019 | Bagherinia | G06T 7/12 |
| 2019/0209006 A1* | 7/2019 | Abou Shousha | A61B 3/1005 |
| 2019/0343390 A1* | 11/2019 | Boppart | A61B 5/0066 |

\* cited by examiner

SEGMENTATION IN OPTICAL COHERENCE TOMOGRAPHY IMAGING

TECHNICAL FIELD

Embodiments disclosed herein are related to devices, systems, and methods for improving segmentation performance in Optical Coherence Tomography (OCT) imaging.

BACKGROUND

Current ophthalmic refractive surgical methods, such as cataract surgery, intra-corneal inlays, laser-assisted in situ keratomileusis (LASIK), and photorefractive keratectomy (PRK), rely on ocular biometry data to prescribe the best refractive correction. Historically, ophthalmic surgical procedures used ultrasonic biometry instruments to image portions of the eye. In some cases, these biometric instruments generated a so-called A-scan of the eye: an acoustic echo signal from all interfaces along an imaging axis that was typically aligned with an optical axis of the eye: either parallel with it, or making only a small angle. Other instruments generated a so-called B-scan, essentially assembling a collection of A-scans, taken successively as a head or tip of the biometry instrument was scanned along a scanning line. This scanning line was typically lateral to the optical axis of the eye. These ultrasonic A- or B-scans were then used to measure and determine biometry data, such as an ocular axial Length, an anterior depth of the eye, or the radii of corneal curvature.

In some surgical procedures, a second, separate keratometer was used to measure refractive properties and data of the cornea. The ultrasonic measurements and the refractive data were then combined in a semi-empirical formula to calculate the characteristics of the optimal intraocular lens (IOL) to be prescribed and inserted during the subsequent cataract phaco surgery.

More recently, ultrasonic biometry devices have been rapidly giving way to optical imaging and biometry instruments that are built on the principle of Optical Coherence Tomography (OCT). OCT is a technique that enables micron-scale, high-resolution, cross-sectional imaging of the human retina, cornea, or cataract. OCT technology is now commonly used in clinical practice, with such OCT instruments are now used in 80-90% of all IOL prescription cases. Among other reasons, their success is due to the non-contact nature of the imaging and to the higher precision than that of the ultrasound biometers.

Accurate segmentation of layer boundaries in the OCT image of the eyes is an important step to transform qualitative images into quantitative measurements that can be used for diagnosis and surgical guidance. This segmentation can be done manually, but the manual process is time consuming and subjective. Accordingly, automatic layer segmentation algorithms have been developed. However, OCT segmentation remains challenging, due to speckles in the OT images and complicated pathologies in some eyes. For instance, because of speckles, the continuous thin boundaries between different types of tissue may appear discontinuous and much thicker in the OCT image. Moreover, in pathological eyes, such as those with dense cataracts, the scattering gradients inside the crystalline lens can reduce the contrast of other edges substantially, in particular for a weak contrast edge like the boundary between the posterior lens (capsule) and the vitreous. With conventional segmentation methods, the segmentation accuracy is reduced or impossible for some of these cases. Accordingly, further improvements in segmentation techniques are needed.

SUMMARY

Disclosed herein are techniques and apparatus for improving OCT segmentation performance, in particular for edges that have a weak contrast, such as the edge between the posterior lens (capsule) and the vitreous. Embodiments of these techniques and apparatus use feature integration to automatically minimize noise features so as to enhance the feature of the true edge. As a result, the segmentation performance is improved.

More particularly, embodiments of the presently disclosed techniques include a method for improving segmentation in OCT imaging, where the method comprises obtaining an OCT image of imaged tissue, generating a first feature image for at least a portion of the OCT image, and generating a second feature image for at least the portion of the OCT image, based on either the OCT image or the first feature image, by integrating image data in a first direction across the OCT image or first feature image. A third feature image is generated as a mathematical function of the first and second feature images, and layer segmentation for the OCT image is performed, based on the third feature image.

Also described in detail below are embodiments of OCT imaging apparatus configured to carry out the method summarized above, or variants thereof.

DETAILED DESCRIPTION

In the following description, specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

Figure 1:
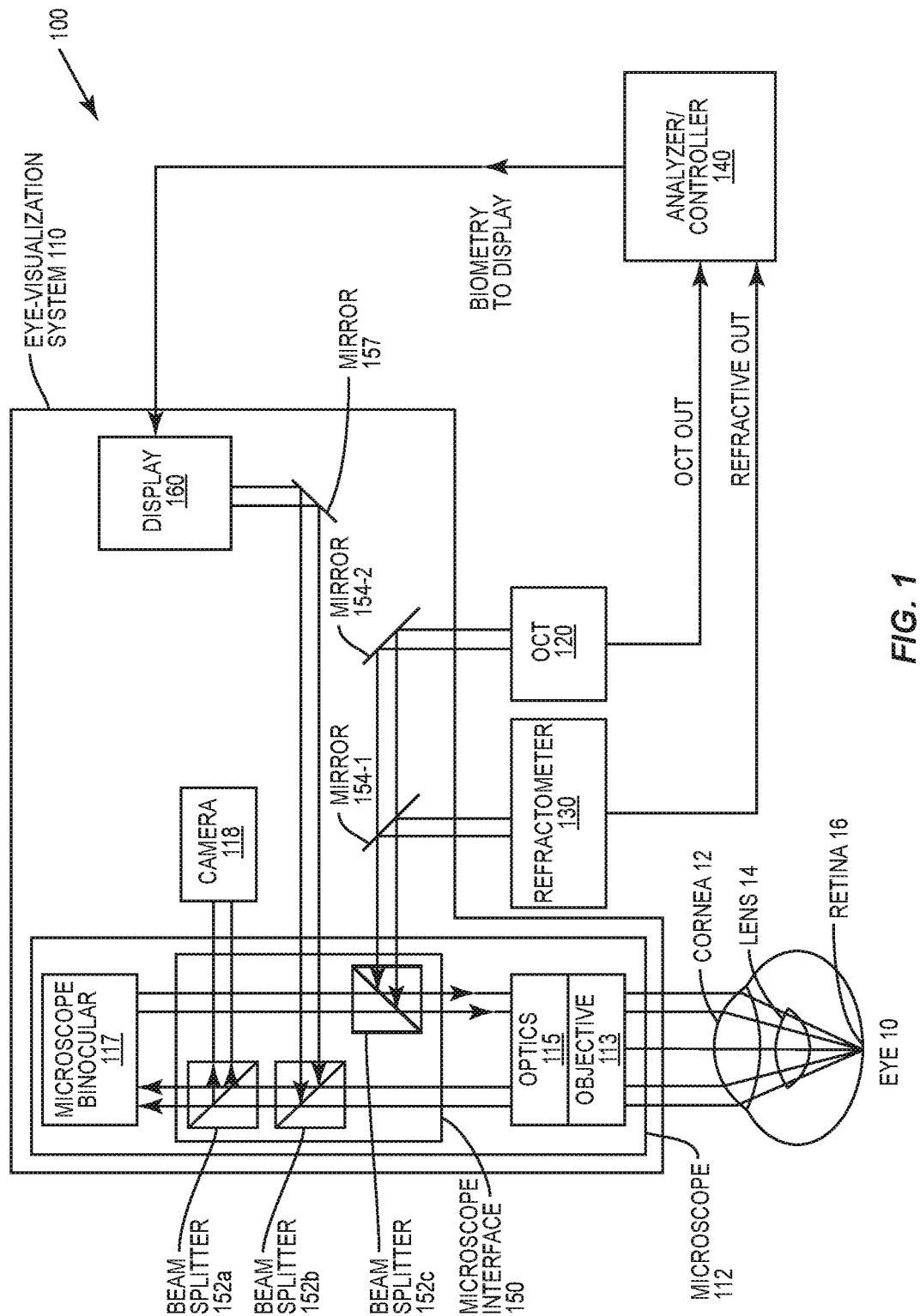
FIG. 1 is a diagram illustrating an Optical Coherence Tomography (OCT) system, consistent with some embodiments.

Embodiments of the presently disclosed techniques and apparatus may be employed in both microscope-mounted and microscope-integrated Optical Coherence Tomography (OCT) systems. FIG. 1 illustrates an example of a microscope-integrated OCT system 100, and is presented to illustrate the basic principles of OCT. It will be appreciated that OCT equipment configured to carry out the techniques described herein may vary from the example illustrated in FIG. 1 in various ways that are already known to the industry.

System 100 includes an eye-visualization system 110, configured to provide a visual image of an imaged region in an eye 10, an Optical Coherence Tomographic (OCT) imaging system 120, configured to generate an OCT image of the imaged region; a refractometer 130, configured to generate a refractive mapping of the imaged region; and an analyzer 140, configured to determine refractive characteristics of the eye based on the OCT image and the refractive mapping. It will be appreciated that the OCT imaging system 120, the refractometer 130, and the analyzer/controller 140 can be integrated into the eye visualization system 110.

Figure 2:
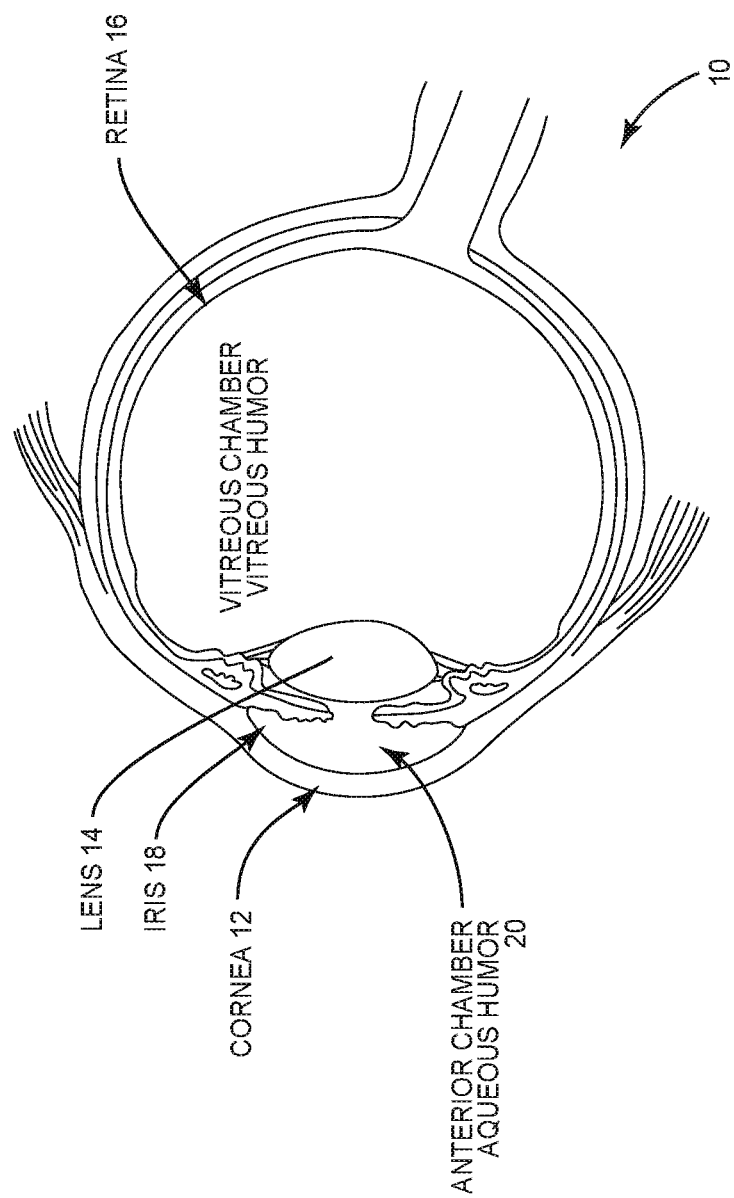
FIG. 2 is a schematic diagram of an eye.

The imaged region can be a portion or a region of the eye 10, such as a target of a surgical procedure. FIG. 2 is a cross sectional diagram showing features of an eye 10. In a corneal procedure, the imaged region can be a portion of a cornea 12. In a cataract surgery, the imaged region can be a capsule and the (crystalline) lens 14 of the eye. The imaged region may also include the anterior chamber 20 of the eye, the cornea 12, the lens 14, and the iris 18. Alternatively, the imaged region may cover the full eye, including the cornea 12, the lens 14, the iris 18, and the retina 16. In a retinal procedure, the imaged region can be a region of the retina 16. Any combination of the above imaged regions can be an imaged region as well.

The eye-visualization system 110 can include a microscope 112. In some embodiments, it can include a slit-lamp. The microscope 112 can be an optical microscope, a surgical microscope, a video-microscope, or a combination thereof. In the embodiment of FIG. 1, the eye-visualization system 110 (shown in thick solid line) includes the surgical microscope 112, which in turn includes an objective 113, optics 115, and a binocular or ocular 117. The eye-visualization system 110 can also include a camera 118 of a video microscope.

System 100 further includes the Optical Coherence Tomographic (OCT) imaging system 120. The OCT imaging system 120 can generate an OCT image of the imaged region. The OCT imaging system can be configured to generate an A-scan or a B-scan of the imaged region. The OCT image or image information can be outputted in an "OCT out" signal that can be used by analyzer 140, for example, in combination with an outputted "Refractive out" signal to determine biometric or refractive characteristics of the eye.

OCT imaging system 120 can include an OCT laser operating at a wavelength range of 500-2,000 nm, in some embodiments at a range of 900-1,400 nm. The OCT imaging system 120 can be a time-domain, a frequency-domain, a spectral-domain, a swept-frequency, or a Fourier Domain OCT system 120.

In various embodiments, part of the OCT imaging system 120 can be integrated into the microscope, and part of it can be installed in a separate console. In some embodiments, the OCT portion integrated into the microscope can include only an OCT light source, such as the OCT laser. The OCT laser or imaging light, returned from the eye, can be fed into a fiber and driven to a second portion of the OCT imaging system 120, an OCT interferometer outside the microscope. The OCT interferometer can be located in a separate console, in some embodiments, where suitable electronics is also located to process the OCT interferometric signals.

The OCT laser may have a coherence length that is longer than an extent of an anterior chamber of the eye, such as the distance between a corneal apex to a lens apex. This distance is approximately 6 mm in most patients, thus such embodiments can have a coherence length in the 4-10 mm range. Other embodiments can have a coherence length to cover an entire axial length of the eye, such as 30-50 mm. Yet others can have an intermediate coherence length, such as in the 10-30 mm range, finally some embodiments can have a coherence length longer than 50 mm. Some swept-frequency lasers are approaching these coherence length ranges. Some Fourier Domain Mode Locking (FDML) lasers, vertical-cavity surface-emitting laser (VCSEL)-based, polygon-based or MEMS-based swept lasers are already capable of delivering a laser beam with a coherence length in these ranges.

The example illustrated as system 100 further includes a refractometer 130 to generate a refractive mapping of the imaged region. The refractometer 130 may be any of the widely used types, including a laser ray tracer, a Shack-Hartmann, a Talbot-Moire, or another refractometer. The refractometer 130 can include a wavefront analyzer, an aberration detector, or an aberrometer. Some references use these terms essentially interchangeably or synonymously. A dynamic range of the refractometer 130 can cover both phakic and aphakic eyes, i.e., the eyes with and without the natural lens.

In some systems, the OCT imaging system 120 and the refractometer 130 can be integrated via a microscope interface 150 that can include a beam splitter 152c to provide an optical coupling into the main optical pathway of the microscope 112 or slit-lamp. A mirror 154-1 can couple the light of the refractometer 130 into the optical path, and a mirror 154-2 can couple the light of the OCT 120 into the optical path. The microscope interface 150, its beam splitter 152c, and mirrors 154-1/2 can integrate the OCT imaging system 120 and the refractometer 130 with the eye-visualization system 110.

In some embodiments, where the OCT imaging system 120 operates in the near infrared (IR) range of 900-1,400 nm, and the refractometer operates in the 700-900 nm range, the beam splitter 152c can be close to 100% transparent in the visible range of 400 nm-700 nm, and close to 100% reflective in the near-IR range of 700-1,400 nm range for high efficiency and low noise operations. Likewise, in a system where the mirror 154-1 redirects light into the refractometer 130, the mirror 154-1 can be close to 100% reflective in the near IR range of 700-900 nm, and the mirror 154-2 can be close to 100% refractive in the near IR range of 900-1,400 nm, redirecting to the OCT imaging system 120. Here, "close to 100%" can refer to a value in the 50-100% range in some embodiments, or to a value in the 80-100% range in others. In some embodiments, the beam splitter 152c can have a reflectance in the 50-100% range for a wavelength in the 700-1,400 nm range, and a reflectance in the 0-50% range for a wavelength in the 400-700 nm range.

FIG. 1 shows that the system 100 can include a second beam splitter 152b, in addition to the beam splitter 152c. The beam splitter 152c directs light between the objective 113 and the integrated OCT 120/refractometer 130 ensemble. The beam splitter 152b can direct light between a display 160 and the binocular 117. A third beam splitter 152a can direct light to the camera 118.

The analyzer, or controller, 140 can perform the integrated biometrical analysis based on the received OCT and refractive information. The analysis can make use of a wide variety of well-known optical software systems and products, including ray tracing software and computer-aided design (CAD) software. The result of the integrated biometry can be (1) a value of the optical power of portions of the eye and a corresponding suggested or prescribed diopter for a suitable IOL; (2) a value and an orientation of an astigmatism of the cornea, and suggested or prescribed toric parameters of a toric IOL to compensate this astigmatism; and (3) a suggested or prescribed location and length of one or more relaxing incisions to correct this astigmatism, among others.

The analyzer 140 can output the result of this integrated biometry towards the display 160, so that the display 160 can display these results for the surgeon. Display 160 can be an electronic video-display or a computerized display, associated with the eye-visualization system 110. In other embodiments, the display 160 can be a display in close proximity of the microscope 112, such as attached to the outside of the microscope 112. Finally, in some embodiments, display 160 can be a micro-display, or heads-up display, that projects the display light into the optical pathway of the microscope 112. The projection can be coupled into the main optical pathway via a mirror 157. In other embodiments, the entire heads-up display 160 can be located inside the microscope 112, or integrated with a port of the microscope 112.

Anatomically, the iris 18 is in contact or in close proximity to the crystalline or intraocular lens (capsule) 14, which can cause difficulties when only the lens information is of interest to the user. For instance, when building a customized eye model, it is crucial to include the shape of the anterior lens. However, with the iris 18 closely in contact with the lens surface, a mixture of the anterior iris and the anterior lens can be misinterpreted as the anterior lens, which can then undermine the performance of the eye model. Therefore, detecting iris is critical in order to extract the lens information accurately.

As briefly discussed above, OCT segmentation is challenging mainly due to speckles and complicated pathologies. For instance, due to speckles, the continuous thin boundaries between different types of tissue become discontinuous and much thicker. Moreover, in pathological eyes, such as dense cataract, the scattering gradients inside the crystalline lens can reduce the contrast of other edges substantially, in particular, for a weak contrast edge like the boundary between posterior lens (capsule) and the vitreous. With conventional segmentation method, the accuracy is largely reduced for these cases or it becomes impossible to segment.

Described herein are techniques and apparatus that use feature integration to automatically minimize noise features, so as to enhance the feature of the true edge. As a result, segmentation performance is improved.

Figure 3:
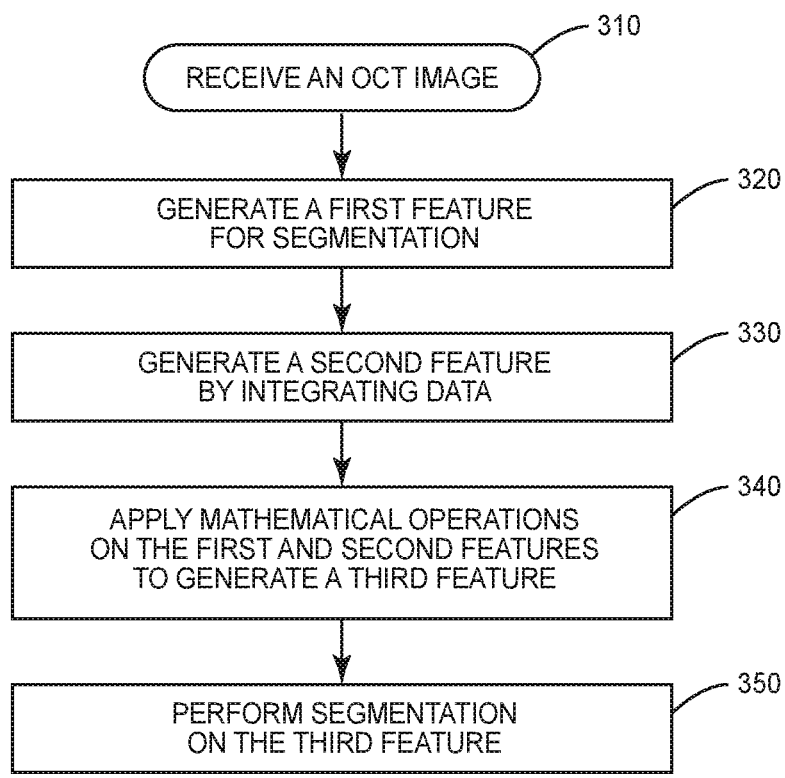
FIG. 3 is a process flow diagram illustrating an example method for improving segmentation in OCT imaging.

FIG. 3 is a flow chart illustrating an example method for improving segmentation in OCT imaging. As shown at block 310, the method includes first obtaining an OCT image. As shown at block 320, a first feature image is generated for image segmentation, for at least a portion of the OCT image. This may involve, for example, generating gradients along the row direction, or the column direction, or both. It is also possible to use other convolutional kernels, such as those kernels learned from neural networks, to generate this first feature.

As shown at block 330, integration of image data is performed along a direction that crosses an edge of interest at an angle, to generate a second feature image. This angle can be any number from 0.1 degree to 179.9 degree. The integration can be based on the features generated in the step shown at block 320, in some embodiments. It is also possible that the integration can be based on features different from those generated in the step shown at block 320, such as the original OCT intensity.

As shown at block 340, mathematical operations are applied on the first and second feature images, to generate a third feature image. In some embodiments, for example, the mathematical operation can be simple subtraction. In this case, the new feature image is derived by subtracting all or parts of the second feature image, as generated according to the step shown at block 330, from the first feature image, as generated according to the step shown at block 320.

Finally, as shown at block 350, layer segmentation for the OCT image is performed, based on the third feature image. Because of the integration process, the segmentation contrast is enhanced, and segmentation accuracy is improved.

As suggested above, generating the first feature image for at least the portion of the OCT image comprises calculating gradients along a row direction of the OCT image, or a column direction of the OCT image, or both, to obtain the first feature image. In some embodiments, the OCT image comprises a plurality of A-lines and generating the second feature image comprises, for each of the A-lines, integrating image data from the OCT image or the first feature image in a direction along the A-line, from a bottom edge of the OCT image or the first feature image towards the opposite edge. In some embodiments, as noted above, generating the third feature image comprises subtracting the second feature image from the first feature image. Once the layer segmentation has been performed for the OCT image, a visual representation of the OCT image may be displayed, where visual representation including an indication of the layer segmentation.

Figure 4:
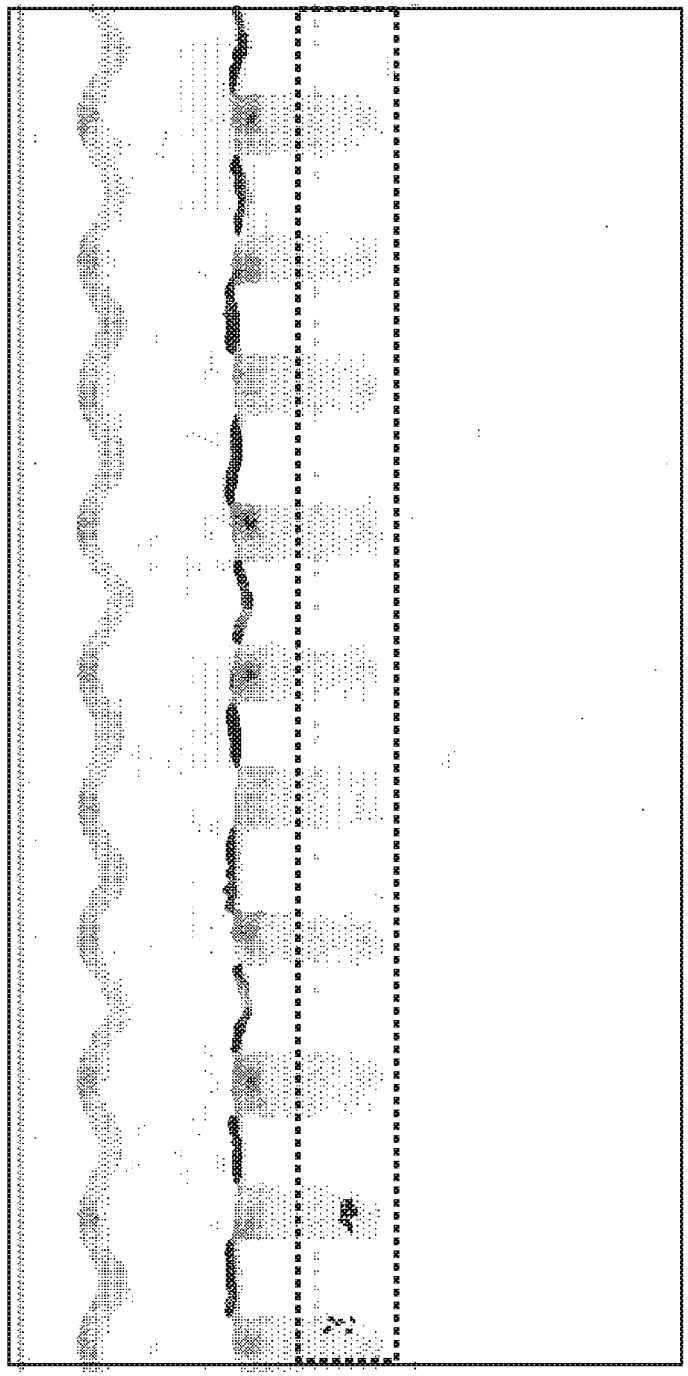
FIG. 4 illustrates an example OCT image.

FIGS. 4-9 illustrate an example use of the method illustrated in FIG. 3 and discussed above. FIG. 4 illustrates an example OCT image comprising many A-lines indexed from left to right, where A-lines extend from the top of the image to the bottom. It is noteworthy that the techniques described herein on any OCT scan pattern, such as line scan, raster scan, circular scan, spiral scan, lissajous scan, a flower scan, etc. FIG. 10 illustrates the scan pattern used to obtain the OCT image of FIG. 4. The scan starts at one point of the scan pattern and proceeds through each petal of the pattern, until coming back to the same point. In FIG. 4, the OCT scan generally depicts the cornea, iris, and lens (from top to bottom).

In FIG. 4, the edge of interest, highlighted in the dashed box, shows a poor contrast. This edge will be the focus of the improved layer segmentation in this example.

Figure 5:
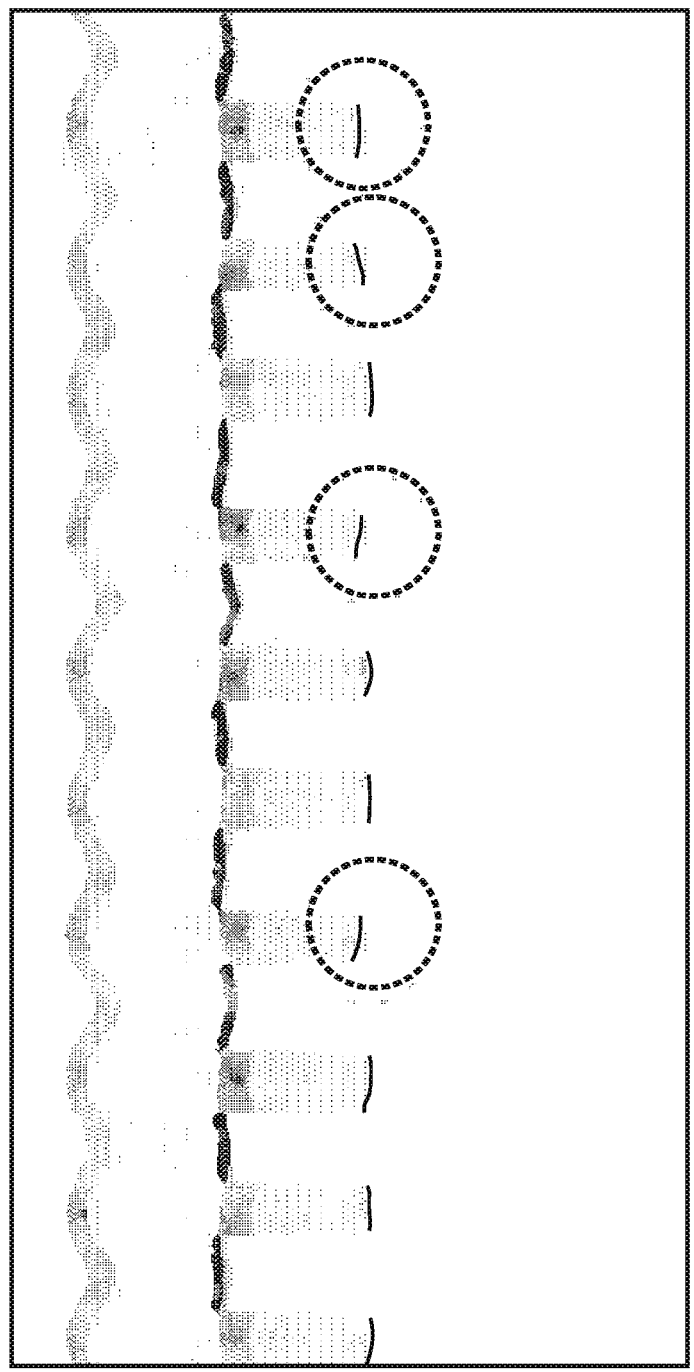
FIG. 5 shows the result of a conventional segmentation method performed on the OCT image of FIG. 4.

FIG. 5 shows the result of a conventional segmentation approach. Due to the strong scattering gradient inside the crystalline lens, the segmented edge between posterior lens (capsule) and vitreous has incorrectly been placed inside the lens at several places in the OCT image, as highlighted in the dashed circles.

Figure 6:
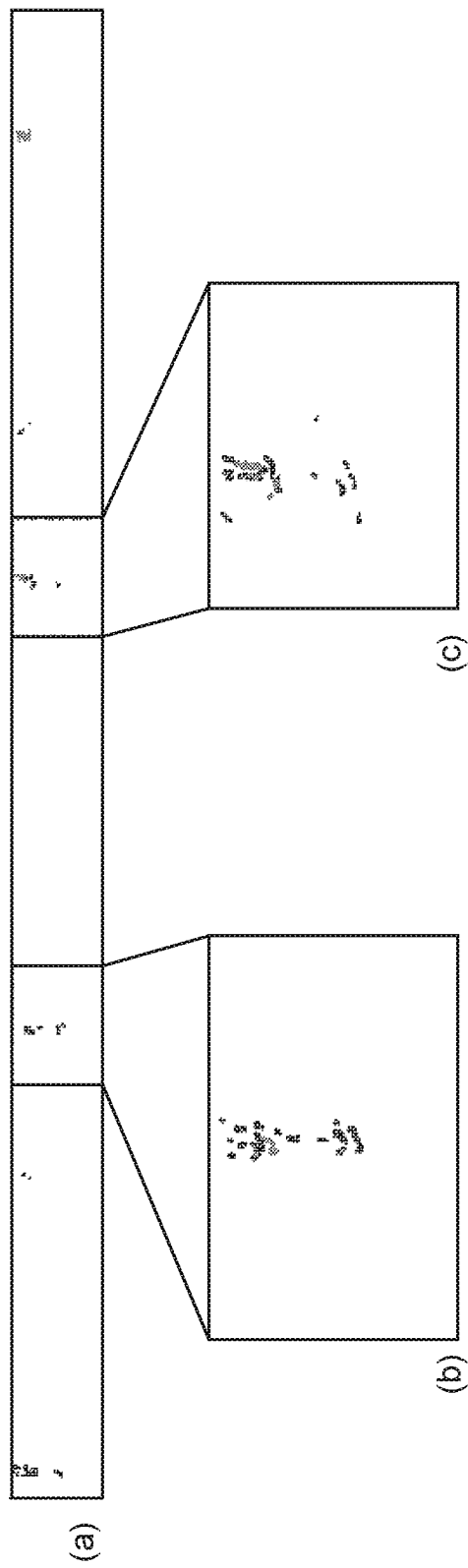
FIG. 6 illustrates first features generated from the OCT image of FIG. 4.

FIGS. 6-9 illustrate the performance of the technique described above, in connection with FIG. 3. Once an OCT image is obtained, e.g., as shown in FIG. 4, a first feature image for segmentation is generated. In FIG. 6, section (a) shows the gradient feature image of the region highlighted in the dashed box in FIG. 4. In FIG. 6, the sections (b) and (c) each show a zoomed-in view of gradient features. As can be seen in sections (b) and (c), speckles in the original OCT image creates substantial discontinuities and non-uniformity on the edge. Moreover, strong gradient features inside the lens reduce the contrast of the edge between posterior lens (capsule) and the vitreous.

Figure 7:
FIG. 7 illustrates second features generated by integration from the feature image of FIG. 6.

FIG. 7 shows the image result of a second-integrated-feature, in this case based on the features generated and displayed in FIG. 6, section (a). It is worth noting, however, that the integrated features can also be generated based on the original OCT image. In this example, the integration was started from the bottom of the image and along each A-line. For instance, each pixel in FIG. 7 shows the accumulated intensity value from the bottom of the image to that pixel along that A-line.

Figure 8:
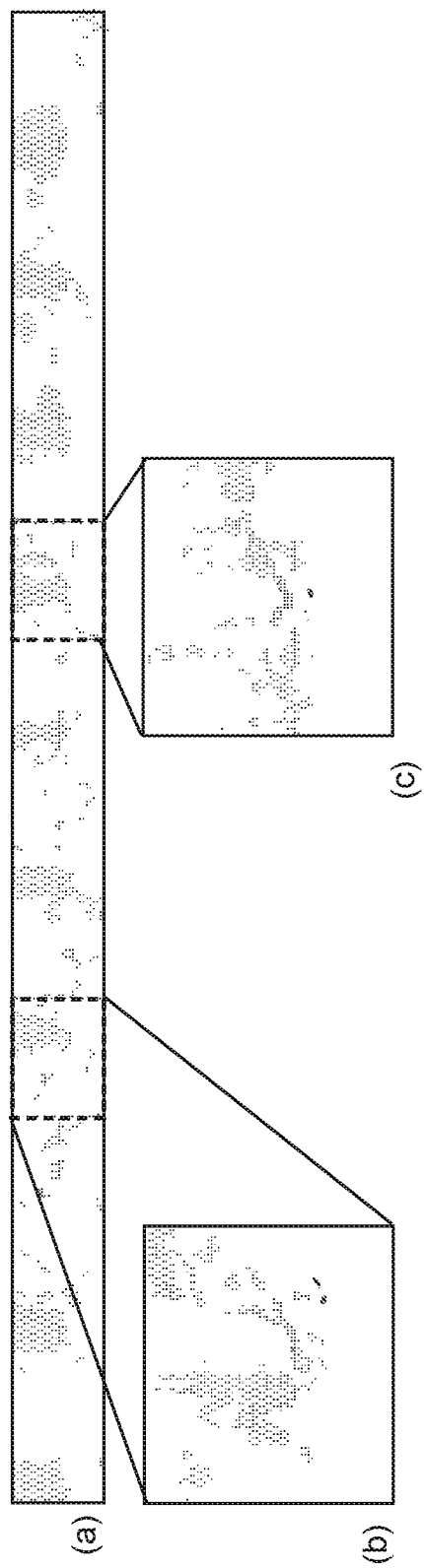
FIG. 8 illustrates third features generated from the first and second features of FIG. 6 and FIG. 7.

After this second integrated feature image is generated, one or more mathematical operations can be applied to the first and second feature images, to generate a third feature image, as shown in FIG. 8, section (a). FIG. 8, section (b) and FIG. 8, section (c) show enlarged view of two regions, corresponding to the same regions shown in FIG. 6 section (a) and FIG. 6 section (c), respectively. It can be seen that the noise features inside the lens are largely reduced.

Figure 9:
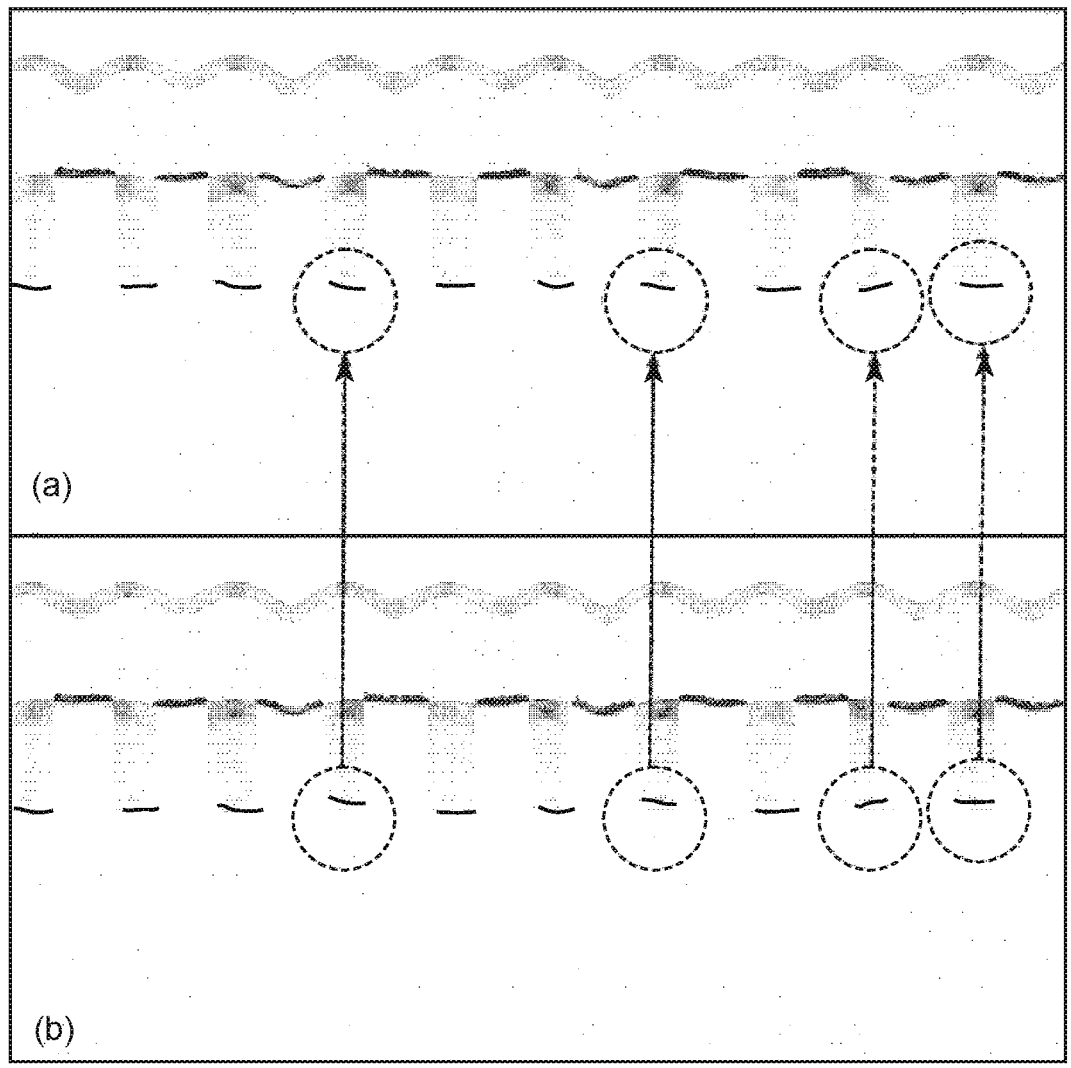
FIG. 9 illustrates the result of layer segmentation performed on the third feature image of FIG. 8.
Figure 10:
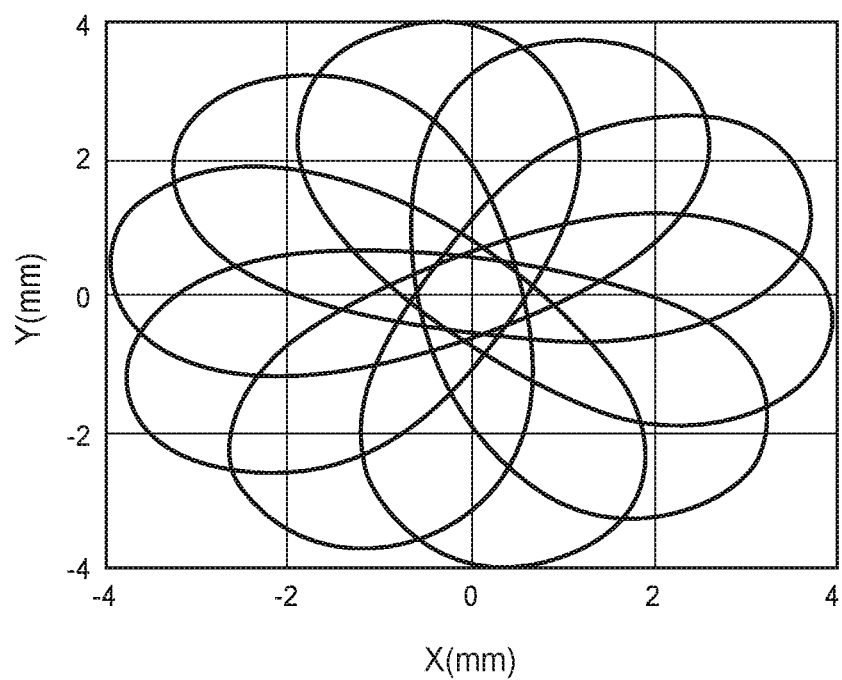
FIG. 10 illustrates an example OCT scan pattern.

FIG. 9, section (a) shows the segmentation result based on the new features shown in FIG. 6. Note that any of a variety of segmentation algorithms may be applied to the third feature image to perform the layer segmentation. In the dashed boxes of FIG. 9, section (a), the segmented edges reflect the true location of the boundary between the posterior lens (capsule) and the vitreous. Direct comparison can be visualized by comparing FIG. 9, section (b), which shows the original segmentation, to FIG. 9, section (a), which shows the segmentation (using the same segmentation algorithm) as performed on the feature image of FIG. 8.

The techniques described herein may be performed using OCT image obtained from an OCT imaging apparatus, e.g., from an apparatus like that illustrated in FIG. 1. These techniques may be integrated into the OCT imaging apparatus itself, to produce an imaging system that integrates OCT imaging and the iris detection techniques described herein.

Accordingly, some embodiments of the present invention include an OCT image processing apparatus, the OCT image processing apparatus comprising a communications interface for obtaining an OCT image of image tissue, obtained from a scan of the eye, and a processing circuit operatively coupled to the communications interface and configured to carry out one or more of the techniques described herein. This OCT image processing apparatus may correspond to the analyzer/controller 140 pictured in FIG. 1, in some embodiments.

The OCT data obtained by the OCT image processing apparatus in these various embodiments comprises a plurality of A-lines, some of which pass through the iris and the lens of the eye and some of which pass through the lens but not the iris. The processing circuit may comprise one or more microprocessors, microcontrollers, or the like, and associated memory storing program code for execution by the microprocessors, microcontrollers, or the like, with the program code comprising computer program instructions for carrying out all or the techniques described herein, and may also or instead comprise other digital logic configured to carry out all or parts of any of the techniques described herein. The processing circuit is thereby configured to generate a first feature image for at least a portion of the OCT image, generate a second feature image for at least the portion of the OCT image, based on either the OCT image or the first feature image, by integrating image data in a first direction across the OCT image or first feature image, and generate a third feature image as a mathematical function of the first and second feature images. The processing circuit is further configured to perform layer segmentation for the OCT image, based on the third feature image.

In some embodiments, the OCT image processing apparatus further comprises or is associated with a video display, e.g., the display 160 illustrated in FIG. 1, and the processing circuit is further configured to use or cause the display to display a visual representation of the OCT image, the visual representation including an including an indication of the layer segmentation.

The OCT image processing apparatus described above may be configured to carry out one or several of the variants of the techniques described above, in various embodiments. Accordingly, in some embodiments of the OCT image processing apparatus, the processing circuit is configured to generate the first feature image for at least the portion of the OCT image by calculating gradients along a row direction of the OCT image, or a column direction of the OCT image, or both, to obtain the first feature image. In some embodiments, the processing circuit is configured to generate the second feature image by, for each of the A-lines, by integrating image data from the OCT image or the first feature image in a direction along the A-line, from a bottom edge of the OCT image or the first feature image towards the opposite edge. In some embodiments, the processing circuit is configured to generate the third feature image by subtracting the second feature image from the first feature image.

The specific embodiments described above illustrate but do not limit the invention. It should also be understood that numerous modifications and variations are possible in accordance with the principles of the present invention, as described above and as claimed below.

What is claimed is:

1. A method for improving segmentation in optical coherence tomography (OCT) imaging, the method comprising:
    obtaining an OCT image of imaged tissue, wherein the OCT image comprises a plurality of A-lines;
    generating a first feature image for at least a portion of the OCT image;
    generating a second feature image for at least the portion of the OCT image, based on either the OCT image or the first feature image, by integrating image data in a first direction across the OCT image or first feature image, wherein generating the second feature image comprises, for each of the A-lines, integrating image data from the OCT image or the first feature image in a direction along the A-line, from a bottom edge of the OCT image or the first feature image towards the opposite edge;
    generating a third feature image as a mathematical function of the first and second feature images; and
    performing layer segmentation for the OCT image, based on the third feature image.

2. The method of claim 1, wherein generating the first feature image for at least the portion of the OCT image comprises calculating gradients along a row direction of the OCT image, or a column direction of the OCT image, or both, to obtain the first feature image.

3. The method of claim 1, wherein generating the third feature image comprises subtracting the second feature image from the first feature image.

4. The method of claim 1, further comprising displaying a visual representation of the OCT image, the visual representation including an indication of the layer segmentation.

5. An Optical Coherence Tomography (OCT) imaging apparatus, comprising:
    a communication interface configured to obtain an OCT image of imaged tissue, wherein the OCT image comprises a plurality of A-lines; and a processing circuit operatively coupled to the communication interface and configured to:
generate a first feature image for at least a portion of the OCT image;
generate a second feature image for at least the portion of the OCT image, based on either the OCT image or the first feature image, by integrating image data in a first direction across the OCT image or first feature image, wherein the processing circuit is configured to generate the second feature image by, for each of the A-lines, by integrating image data from the OCT image or the first feature image in a direction along the A-line, from a bottom edge of the OCT image or the first feature image towards the opposite edge;
generate a third feature image as a mathematical function of the first and second feature images; and
perform layer segmentation for the OCT image, based on the third feature image.

6. The OCT imaging apparatus of claim 5, wherein the processing circuit is configured to generate the first feature image for at least the portion of the OCT image by calculating gradients along a row direction of the OCT image, or a column direction of the OCT image, or both, to obtain the first feature image.

7. The OCT imaging apparatus of claim 5, wherein the processing circuit is configured to generate the third feature image by subtracting the second feature image from the first feature image.

8. The OCT imaging apparatus of claim 5, further comprising a display, wherein the processing circuit is configured to use or cause the display to display a visual representation of the OCT image, the visual representation including an indication of the layer segmentation.

* * * * *